United States Patent [19]

Kabeta

[11] Patent Number: 4,990,641
[45] Date of Patent: Feb. 5, 1991

[54] ORGANOSILICON COMPOUND AND ITS PREPARING METHOD

[75] Inventor: Keiji Kabeta, Gunma, Japan

[73] Assignee: Toshiba Silicone Co., Ltd., Tokyo, Japan

[21] Appl. No.: 376,834

[22] Filed: Jul. 7, 1989

[30] Foreign Application Priority Data

Jul. 8, 1988 [JP] Japan ................. 63-170475
Jul. 8, 1988 [JP] Japan ................. 63-170476

[51] Int. Cl.$^5$ ............................................. C07F 7/10
[52] U.S. Cl. ..................................................... 556/419
[58] Field of Search ........................................... 556/419

[56] References Cited

U.S. PATENT DOCUMENTS 4,777,276 10/1988 Rasmussen et al. .............. 556/419
4,837,290 6/1989 Rasmussen et al. .......... 556/419 X
4,888,406 12/1989 Oksurgi et al. ................. 556/419 X Primary Examiner—Paul F. Shaver
Attorney, Agent, or Firm—Flynn, Thiel, Boutell & Tanis

[57] ABSTRACT

A new organosilicon compound is defined by the formula (1):

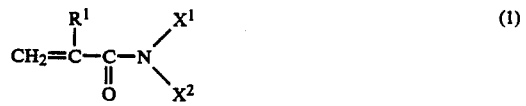

in which $R^1$ is a hydrogen atom or a methyl gorup, $X^1$ and $X^2$ each independently are —$CH_2CH=CH_2$ or —$(CH_2)_2SiR^2{}_nY_{3-n}$, provided at least one of them —$(CH_2)_bSiR^2{}_nY_{3-n}$, $R^2$ is a substituted or non-substituted monovalent hydrocarbon group, Y is an alkoxy group or a halogen atom, and n is zero, 1 or 2.

9 Claims, 2 Drawing Sheets

ORGANOSILICON COMPOUND AND ITS PREPARING METHOD

TECHNICAL FIELD OF THE INVENTION

This invention relates to a new organosilicon compound containing unsaturated groups that is useful as a modifier for a composite material of organic polymers and inorganic fillers, as well as a crosslinking agent and modifier for organic polymers.

DESCRIPTION OF THE PRIOR ART

Examples of organosilicon compounds possessing vinyl groups such as vinyltrichlorosilane, vinyltriethoxysilane, vinylmethyldiethoxysilane, vinyltris(methoxydiethoxy)silane, γmethacryloxypropyltrimethoxysilane, and γmethacryloxypropylmethyldimethoxysilane are already widely known. These silanes are also widely known as silane coupling agents, and are effective in improving the physical properties of composites of organic polymers and inorganic fillers, as well as improving the surface properties and adhesive properties, through surface treatment, of solid and inorganic fillers. In addition, they are also widely used as crosslinking agents and modifiers for various organic polymers.

However, it is known that vinyl groups bonded to silicon atoms differ in reactivity in comparison to vinyl groups bonded to carbon atoms. As a result, methods which introduce vinylsilane into organic polymers are restricted, as well as being difficult. Further, in the case of vinylsilane, there is also the problem of its compatibility with organic compounds and organic polymers being restricted.

In addition, there are problems with silanes possessing methacryloxy groups, with respect to their water resisting properties when used in composites, and with their crosslinking capabilities when used as crosslinking agents.

In addition, although the compound N-allyl-N,N-bis[3-(triethoxysilyl)propyl]amine is widely known (Zh. Obshch. Khim., 53, 1591–6, (1983)), since the reactivity of the allyl group is slightly lower than that of vinylsilanes, various factors made it unsatisfactory for use as a silane coupling agent or crosslinking agent.

Organic silicon compounds which possess two types of functional groups within the same molecule are widely known. These compounds are used as silane coupling agents, raw materials of various chemical compounds, monomers for the preparation of silicon-containing polymer compounds, crosslinking agents and modifiers, etc. by taking advantage of the reactivities or differences in reactivities of their respective functional groups. For example, organosilicon compounds which are used as silane coupling agents possess carbon functional groups which bind to organic materials and silicon functional groups which react with and bind to inorganic materials within the same molecule. This allows them to strongly bind at the interface of both organic and inorganic materials.

However, current complexing of materials, such as in the case of the IPN system or polymer alloys, is becoming more and more complicated. When used in these types of applications, the previous silane coupling agents became unsatisfactory due to them being unable to couple respective organic substances, thereby resulting in them being ineffective in composite formation.

OBJECTIVES OF THE PRESENT INVENTION

An objective of this invention is to provide a new and useful organosilicon compound which eliminates the problems associated with previous such compounds. In other words, an objective of this invention is to provide a organosilicon compound which is useful as a co-crosslinking agent between copolymerizing monomers and polymers by its improved compatibility with other polymerizing monomers or organic polymers while still possessing highly-reactive double bonds and containing two silylpropyl groups having terminal hydrolytic groups within the same molecule, and moreover, to provide a method for preparing such a compound that is industrially useful.

Another objective of this invention is to provide an organic silicon compound which eliminates the previously described problems, and is suitable for use as a silane coupling agent which strongly binds organic resins and inorganic fillers, as a coupling agent between respective organic compounds, as well as being useful in the preparation, modification and crosslinking reactions of various organic compounds and silicon-containing polymer compounds, and moreover, to provide a method for the manufacture of this compound that is industrially useful.

SUMMARY OF THE INVENTION

The invention provides an organic silicon compound expressed with the formula indicated above in which $R^1$ is hydrogen or a methyl group, $X^1$ and $X^2$ are respectively $-CH_2CH=CH_2$ or $-(CH_2)_3SiR^2{}_nY_{3-n}$, provided that at least one of $X^1$ or $X^2$ is $-(CH_2)_3SiR^2{}_nY_{3-n}$, $R^2$ is a non-substituted or substituted monovalent hydrocarbon group, Y is an alkoxy group or a halogen, and n is zero, 1 or 2.

It is preferable in the formula that $R^2$ is an alkyl group having 1 to 6 carbons, a halogenated alkyl group having 1 to 6 carbons, a cycloalkyl group having 5 to 6 carbons, an aralkyl group, an aryl group, or an alkyl-substituted aryl group having 1 to 3 carbons or a halogen, in other words, a halogenated aryl group, and Y is an alkoxy group having 1 to 4 carbons or a halogen.

In the formula, $R^2$ is a substituted or non-substituted monovalent hydrocarbon group and Y is an alkoxy group or a halogen atom. Examples of the substituted or non-substituted monovalent hydrocarbon group include alkyl groups such as methyl, ethyl, propyl, butyl or hexyl groups, cycloalkyl groups such as cyclopentyl or cyclohexyl groups, aralkyl groups such as 2-phenylethyl, aryl groups such as phenyl or tolyl groups, as well as substituted hydrocarbon groups such as chloromethyl, chlorophenyl or 3,3,3-trifluoropropyl groups. Examples of the alkoxy group include methoxy, ethoxy, propoxy or butoxy groups. Although examples of the halogen atom include fluorine, chlorine, bromine or iodine, in terms of hydrolytic properties and ease of acquisition, a chlorine atom is particularly preferable.

Since the new silane compound of this invention is a compound which contains a (meth)acryl group and two silylpropyl groups to which are attached hydrolytic groups, it can be used in various applications.

In other words, this compound is useful as well as effective as a raw material for the polymerization of organic monomers containing double bonds, as a grafting agent of other organic polymers, as a crosslinking agent, as a coupling agent between organic resins and inorganic fillers, or as a surface treatment agent or adhesion improver for solid surfaces.

Another new silane compound of the present invention is a compound which contains two types of double bonds having different reactivities (in other words, a (meth)acryl group and a allyl group) and a silyl group having a hydrolytic group which allows it to be used in various applications.

In other words, this compound is both useful and effective as a raw material in the synthesis of various organic compounds, as a raw material or modifier of polymer compounds containing silicon, as a coupling agent between two respective organic materials, as a silane coupling agent having suitable water resisting properties between organic resins and inorganic fillers, as well as a surface treatment agent or adhesion improver for solid surfaces, by taking advantage of the reactivities or difference in reactivities of the two types of double bonds having different reactivities.

Specific examples of this invention include Specific Example A which has two silylpropyl groups, and Specific Example B which has one silylpropyl group and a allyl group. Descriptions of each of these are given below with respect to the respective preparation methods in particular.

Specific Example A

As a result of earnest studies on the part of the inventors to obtain an organic compound having the properties described previously, the present invention was completed by forming and isolating the new organosilicon compound expressed with general formula (1):

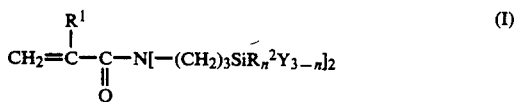

(1)

(where $R^1$, $R^2$, Y and n are as described previously) which contains a highly reactive double bond and two silylpropyl groups to which are attached hydrolytic groups, by the two types of reactions indicated below, the first being the method in which 1 equivalent of the amide compound expressed by the general formula (2):

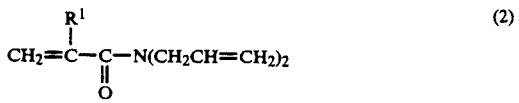

(2)

(where $R^1$ indicates a hydrogen atom or a methyl group) is reacted with roughly 2 equivalents of the silane compound expressed with general formula (3):

$HSiR^2_nY_{3-n}$ (3)

(where $R^2$ is a substituted or non-substituted monovalent hydrocarbon group, Y is an alkoxy group or halogen atom, and n is zero, 1 or 2), or the method in which the acid chloride expressed by the general formula (4):

(4)

(where $R^1$ indicates a hydrogen atom or methyl group) is reacted with the silane compound expressed with general formula (5):

$HN[(CH_2)_3SiR^2_nY_{3-n}]_2$ (5)

(where $R^2$ is a substituted or non-substituted monovalent hydrocarbon group, Y is an alkoxy group or halogen atom, and n is zero, 1 or 2).

In other words, this invention relates to a new organic silicon compound which shows superior reactivity and compatibility with the above organic and inorganic materials, as well as to its method of manufacture.

The silane compounds used in this invention are those compounds expressed with general formula (3) and general formula (5) above.

From among these silane compounds, examples of the compound which corresponds to formula (3) include trimethoxysilane, triethoxysilane, triisopropoxysilane, trichlorosilane, methyldiethoxysilane and dimethylethoxysilane.

In addition, examples of the compounds which corresponds to formula (5) include N,N-bis[3-(trimethoxysilyl)propyl]amine, N,N-bis[3-(triethoxysilyl)propyl]amine, N,N-bis[3-(methyldiethoxysilyl)propyl]amine, and N,N-bis[3-(dimethylethoxysilyl)propyl]amine.

The following provides descriptions of the two types of new synthesis methods of the present invention.

An explanation will first be given regarding the reaction of the N,N-diallyl(meth)acrylamide indicated in formula (2) and the silane compound indicated in formula (3). The catalyst that is used in this reaction is a catalyst that is commonly used in so-called hydrosilation reactions. Although examples of this catalyst include transition metals such as platinum, palladium, nickel, cobalt and ruthenium, as well as their complexes, platinum metals and complexes such as platinum black and chloroplatinic acid are preferable as they are able to result in a reduction in the reaction time as well as resulting in a high yield.

The amount of catalyst is preferably 0.001–5.0 parts by weight per 100 parts by weight of the N,N-diallyl(-meth)acrylamide with 0.01–1.0 parts by weight being more preferable. When the amount of catalyst added is less than 0.001 parts by weight, the reaction speed is insufficient, and even if the catalyst is added in excess of 5.0 parts by weight, not only will there not be any observed improvement in reaction speed, but this is also not preferable in economic terms.

The prepared mole ratio of the silane compound with respect to the N,N-diallyl(meth)acrylamide is roughly 2 moles, with a range of 2.0–3.0 being preferable in terms of practicality. Although the reaction can be carried out within a hydrosilation reaction temperature range of −30° to 150° C., the reaction is normally carried out within a more preferable range of 10° to 110° C. Although the reaction is normally carried out at atmospheric pressure, the pressure may be increased or decreased if necessary.

In addition, although the use of solvents at the time of reaction is not required, the use of a solvent to improve the solubility of the catalyst or control the temperature is allowable. Examples of such solvents include hydrocarbon-type solvents such as toluene, xylene, cyclohexane, n-hexane, n-heptane, naphtha, mineral spirit or petroleum benzene, halogenated hydrocarbon-type solvents such as chloroform, carbon tetrachloride, trichloroethylene, perchloroethylene or 1,1,1-trichloroethane, ether-type solvents such as ethyl ether, tetrahydrofuran or ethylene glycol diethyl ether, ester-type solvents such as ethyl acetate, butyl acetate or amyl acetate, ketone-type solvents such as acetone, methyl ethyl ketone or methyl isobutyl ketone, and aprotic polar solvents such as methyl formamide or dimethylacetoamide.

Since reaction time varies according to the raw materials used, catalyst as well as solvent and reaction temperature, there are no limitations on this parameter in particular. However, reaction conditions are normally set so that the reaction is completed within 0.5 to 6 hours. The reaction is carried out by ordinary methods.

As an example, a method is employed in which a mixture of the N,N-diallyl(meth)acrylamide and catalyst is heated to the specified temperature while stirring followed by dropping in the silane compound indicated in formula (3).

Since the compound is obtained as the result of a reaction of high selectivity, purification of the compound can be performed with currently known methods such as distillation, gas chromatography separation, liquid chromatography separation or column chromatography.

In order to increase the stability of the raw materials and products during the reaction and at the time of purification, the prior addition of known and suitable polymerization inhibitors and oxidation inhibitors is allowable as a routine procedure.

The following provides an explanation of the reaction between the (meth)acryloyl chloride indicated in formula (4) and the silane compound indicated in formula (5). In this reaction, since hydrogen chloride is formed, a dehydrochlorination agent is required. Although the amino group-containing silane compound indicated in formula (5) can be used in excess for this purpose, more typically, another amine which does not react with the (meth)acryloyl chloride is added to the system. Examples of such an amine include pyridine, triethylamine, tributylamine and N-methylmorpholine. The amount of this amine that is added must be equal to or greater than the amount required to neutralize the hydrogen chloride that is produced as a by-product of the reaction. Typically, 1.0–1.5 equivalents of the amine is used with respect to the (meth)acryloyl chloride. If more than this amount is used, the reaction will be slowed and the reaction mixture will become too basic, resulting in the disadvantage of the stability of the products being decreased.

The prepared mole amount of the silane compound of formula (5) with respect to the (meth)acryloyl chloride is roughly 1.0 equivalents, and more preferably, 0.95–1.05 equivalents. If less than 0.95 equivalents of the silane compound is used, there will be an excessive amount of unreacted (meth)acryloyl chloride remaining. Conversely, if more than 1.05 equivalents are added, a large amount of the silane compound will remain unreacted making this disadvantageous in economic terms. However, when using the silane compound as a dehydrochlorination agent as described above, it is only natural that the prepared mole ratio of silane to the (meth)acryloyl chloride be according to the amount of the amine added separately to function as the dehydrochlorination agent. In other words, since it is preferable that the total amount of amine in the reaction mixture be 2.0–2.5 equivalents with respect to the (meth)acryloyl chloride, it is preferable that the silane compound be prepared in an amount that results when the amount of amine that is actually added to serve as the dehydrochlorination agent is subtracted from the above amount.

Although this reaction is typically achieved by dropping the (meth)acryloyl chloride indicated in formula (4) into a solution of the silane compound indicated in formula (5) and the amine used for dehydrochlorination, the use of a solvent is allowed to facilitate temperature control or make stirring easier. Examples of this solvent include hydrocarbon-type solvents such as toluene, xylene, cyclohexane, n-hexane, n-heptane, naphtha, mineral spirit or petroleum benzene, halogenated hydrocarbon-type solvents such as chloroform, carbon tetrachloride, trichloroethylene, perchloroethylene or 1,1,1-trichloroethane, ether-type solvents such as ethyl ether, tetrahydrofuran or ethylene glycol diethyl ether, ester-type solvents such as ethyl acetate, butyl acetate or amyl acetate, and aprotic polar solvents such as dimethylformamide or dimethylacetoamide.

Since the reaction time varies according to the raw materials used, catalyst, as well as the solvent and reaction temperature, there are no limitations on this parameter in particular. However, reaction conditions are typically set so that the reaction is completed within 0.5 to 6 hours.

After the reaction is completed and the hydrochloride of the amine is removed using by filtration or washing, the compound can be purified into the target substance by using known purification procedures similar to those of the previous method. In addition, the prior addition of polymerization inhibitors and oxidation inhibitors similar to those of the previous method during the reaction and at the time of purification is allowed as a routine procedure.

Specific Example B

As a result of earnest studies on the part of the inventors to obtain the organic compound described previously, the present invention was completed by forming and isolating the new organosilicon compound expressed by the general formula (1):

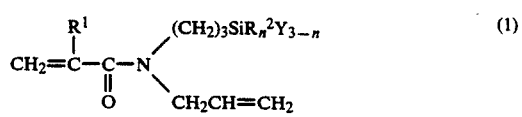

(where $R^1$, $R^2$, Y and n are as described previously) which simultaneously contains two types of double bonds having different reactivities and a silylpropyl group having a hydrolytic group within the same molecule, by the two types of reactions indicated below, a first being the method in which the amide compound expressed by the general formula (2):

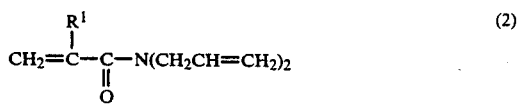

(where $R^1$ indicates a hydrogen atom or a methyl group) is reacted with a silane compound expressed with general formula (3):

$$HSiR^2_nY_{3-n} \quad (3)$$

(where $R^2$ is a substituted or non-substituted monovalent hydrocarbon group, Y is an alkoxy group or halogen atom, and n is zero, 1 or 2), or a method in which the acid chloride expressed by the general formula (4):

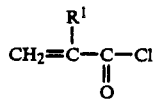

(4)

(where $R^1$ indicates a hydrogen atom or methyl group) is reacted with a silane compound expressed by the general formula (5):

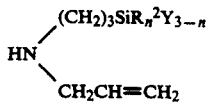

(5)

(where $R^2$ is a substituted or non-substituted monovalent hydrocarbon group, Y is an alkoxy group or halogen atom, and n is zero, 1 or 2).

The silane compounds used in this invention are those compounds expressed by general formula (3) and general formula (5) above.

From among these silane compounds, examples of the compound which corresponds to formula (3) include trimethoxysilane, triethyoxysilane, triisopropoxysilane, trichlorosilane, methyldiethoxysilane and dimethylethoxysilane, methyldichlorosilane and dimethylchlorosilane.

In addition, examples of the compound which corresponds to formula (5) include γ-(N-allyl)aminopropyltrimethoxysilane, γ-(N-allyl)aminopropyltriethoxysilane, γ-(N-allyl)aminopropylmethyldimethoxysilane, and γ-(N-allyl)aminopropyldimethylethoxysilane.

The following provides descriptions of the two types of new synthesis methods of this invention.

A range of 0.5–2.0 for the prepared mole ratio of the silane compound to the N,N-diallyl(meth)acrylamide is preferable, with a range of 0.8–1.2 being more preferable. If less than this amount is used, the raw material of N,N-diallyl(meth)acrylamide will remain in large amounts still unreacted. In addition, if more than this amount is used, the product resulting from two molecules of the organic silicon compound indicated in formula (3) reacting with one molecule of the amide derivative indicated in formula (2) will be formed in large amounts which is unfavorable in obtaining the target compound indicated in formula (1) in terms of both yield and economic factors.

The other reaction conditions are performed in the same manner as that described in Specific Example A.

BRIEF DESCRIPTION OF DIAGRAMS

EXAMPLES OF THE PRESENT INVENTION

Although the following provides an explanation of this invention in greater detail through the use of the following examples, this invention is not limited to such example. Further, the term "parts" used within the examples refers to parts by weight.

EXAMPLE 1

165 parts N,N-diallyl-methacrylamide, 4 parts of 1% chloroplatinic acid-isopropanol solution, and 4 parts of phenothiazine were placed in a 4-necked flask equipped with a thermometer, dropping funnel, stirrer and reflux condenser provided with a calcium chloride tube, and heated to 50° C. while stirring. 295 parts of methyldiethoxysilane was dropped into the mixed solution over a time period of 30 minutes. Following this addition, the mixture was heated further while stirring at 55° C. for 2 hours to bring the reaction to completion. 351 parts of a colorless, transparent liquid was recovered from the obtained reaction mixture by using gas chromatography separation. Infrared absorption spectroscopy, nuclear magnetic resonance spectroscopy, mass spectroscopy and elemental analysis were then performed on this liquid. Those results are indicated in Table 1.

Based on those measurement results, it was confirmed that the compound that was obtained was N,N-bis[3-(methyldiethoxysilyl)propyl]methacrylamide. The yield was 81%, $n_D^{25}=1.4500$ and $d_4^{25}=1.018$.

Figure 1:
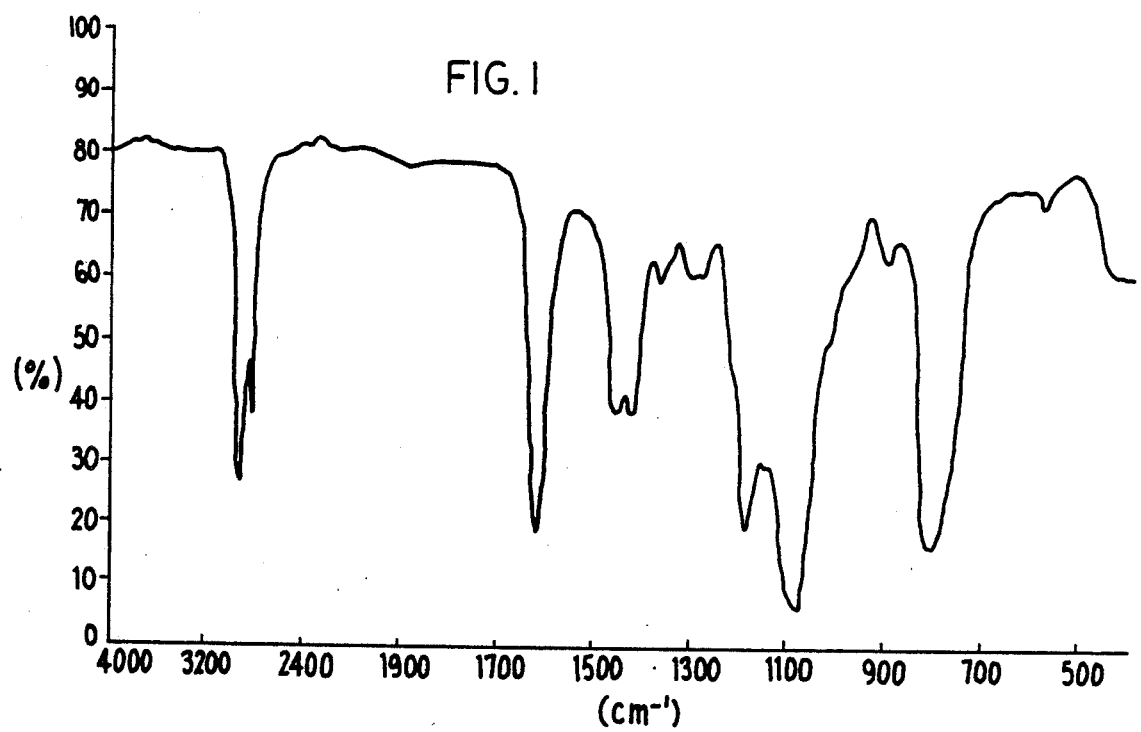
FIG. 1 is the infrared absorption spectrum of the compound prepared in Embodiment 1 and FIG. 2 is the nuclear magnetic resonance spectrum of the same compound.
Figure 2:
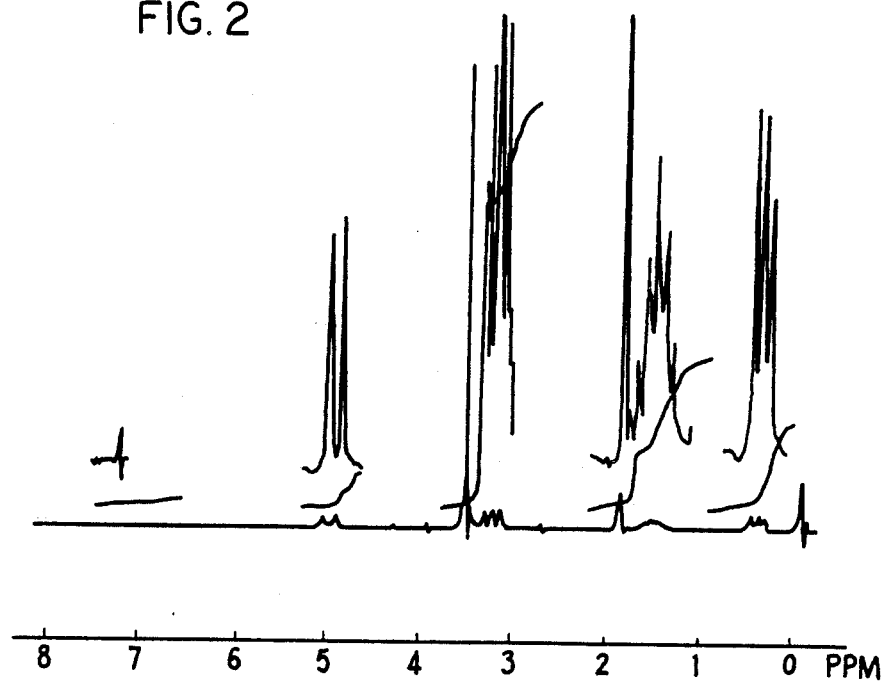

Further, the infrared absorption spectrum and nuclear magnetic resonance spectrum are indicated in FIG. 1 and FIG. 2 respectively.

EXAMPLE 2

298 parts of methyl-diethoxysilane were dropped into a mixed solution of 151 parts of N,N-diallyl-acrylamide, 4 parts of 1% chloroplatinic acid-isopropanol solution, and 4 parts of phenothiazine and allowed to react under the same reaction conditions as those of Example 1. 250 parts of a colorless, transparent liquid was recovered from the obtained reaction mixture by using gas chromatography separation. The same measurements were performed on this liquid as those that were performed in Example 1.

Based on those results, it was confirmed that the compound that was obtained was N,N-bis[3-(methyldiethoxysilyl)propyl]acrylamide. The yield was 60%.

EXAMPLE 3

229 parts of dimethylethoxysilane was dropped into a mixed solution of 165 parts of N,N-diallylmethacrylamide, 4 parts of 1% chloroplatinic acid-isopropanol solution, and 4 parts of phenothiazine and allowed to react under the same reaction conditions as those of Example 1.

273 parts of a colorless, transparent liquid was recovered from the obtained reaction mixture by using gas chromatography separation. The same measurements were performed on this liquid as those that were performed in Example 1.

Based on those results, it was confirmed that the compound that was obtained was N,N-bis[3-(dimethylethoxysilyl)propyl]methacrylamide. The yield was 73%.

EXAMPLE 4

The reaction was carried out using trichlorosilane in place of the methyldiethoxysilane in Example 1.

In other words, 298 parts of trichlorosilane was dropped into a mixed solution of 165 parts of N,N-diallylmethacrylamide, 4 parts of 1% chloroplatinic acid-isopropanol solution, and 4 parts of phenothiazine and allowed to react.

304 parts of a colorless, transparent liquid was recovered from the obtained reaction mixture by using gas chromatography separation. The same measurements were performed on this liquid as those that were performed in Example 1.

Based on those results, it was confirmed that the above obtained compound was N,N-bis[3-(trichlorosilyl) propyl]methacrylamide. The yield was 78%.

EXAMPLE 5

341 parts of N,N-bis(3-trimethoxysilylpropyl)amine, 101 parts of triethylamine, 1160 parts of anhydrous benzene and 0.4 part of phenothiazine as a polymerization inhibitor were placed in a three-necked flask equipped with a thermometer, dropping funnel and reflux condenser to which was attached a calcium chloride tube. 105 parts of methacryloyl chloride dissolved in 230 parts of anhydrous benzene was then dropped into this mixed solution contained in an ice bath over a time period of roughly 20 minutes. The reaction temperature was 5°–15° C. After the addition was completed, the mixture was allowed to react for 2 hours at room temperature. After removing the salt that was formed from the mixture by filtration, the benzene contained in the reaction mixture was removed by distillation in vacuo.

Further, 153 parts of a colorless, transparent liquid was recovered from the obtained oil-like substance by using gas chromatography separation. The same measurements were performed on this liquid as those that were performed in Example 1.

Based on those results, it was confirmed that the above obtained compound was N,N-bis[3-(trimothoxysilyl)propyl]methacrylamide. The yield was 78%.

EXAMPLE 6

9.1 parts of acryloyl chloride dissolved in 23 parts of anhydrous benzene was dropped into a mixture of 341 parts of N,N-bis(3-trimethoxysilylpropyl)amine, 101 parts triethylamine, 1160 part of anhydrous benzene and 0.4 parts of phenothiazine and allowed to react.

324 parts of a colorless, transparent liquid was recovered from the obtained oil-like substance by using gas chromatography separation. The same measurements were performed on this liquid as those that were performed in Example 1.

Based on those results, it was confirmed that the above obtained compound was N,N-bis[3-(trimethoxysilyl)-propyl]acrylamide. The yield was 82%.

TABLE 1

| | example | | | | | |
|---|---|---|---|---|---|---|
| | 1 | 2 | 3 | 4 | 5 | 6 |
| NMR (90MHz,CCl$_4$,δ) | 0.04(s,6H,Si—CH$_3$) 0.30–0.53(m,4H,Si—CH$_2$) 1.20(t,J=7Hz,12H, O—C—CH$_3$) 1.33–1.73(m,4H, Si—C—CH$_2$) 1.85(s,3H,=⟨CH$_3$⟩) 3.22(d,J=7Hz,4H,N—CH$_2$) 3.80(q,J=7Hz,8H,O—CH$_2$) 4.85(br,s,1H,=⟨H⟩) 5.03(br,s,1H,=⟨H⟩) | 0.04(s,6H,Si—CH$_3$) 0.30–0.53(m,4H,Si—CH$_2$) 1.20(t,J=7Hz,12H, O—C—CH$_3$) 1.33–1.73(m,4H,Si—C—CH$_2$) 3.22(d,J=7Hz,4H,N—CH$_2$) 3.80(q,J=7Hz,8H,O—CH$_2$) 5.53(dd,J=3,11Hz,1H,=⟨H⟩) 6.17(dd,J=3,17Hz,1H,=⟨H⟩) 6.47(dd,J=11,17Hz,1H,=⟨H⟩) | 0.03(s,12H,Si—CH$_3$) 0.30–0.53(m,4H,Si—CH$_2$) 1.20(t,J=7Hz,6H,O—C—CH$_3$) 1.33–1.73(m,4H,Si—C—CH$_2$) 1.85(s,3H,=⟨CH$_3$⟩) 3.22(d,J=7Hz,4H,N—CH$_2$) 3.80(q,J=7Hz,4H,O—CH$_2$) 4.85(br,s,1H,=⟨H⟩) 5.03(br,s,1H,=⟨H⟩) | 0.57(t,J=7Hz,4H,Si—CH$_2$) 1.60(quint,J=7Hz,4H, Si—C—CH$_2$) 1.85(s,3H,=⟨CH$_3$⟩) 3.30(t,J=7Hz,4H,N—CH$_2$) 4.85(br,s,1H,=⟨H⟩) 5.03(br,s,1H,=⟨H⟩) | 0.43(t,J=7Hz,4H,Si—CH$_2$) 1.53(quint,J=7Hz,4H, Si—C—CH$_2$) 1.85(s,3H,=⟨CH$_3$⟩) 3.22(t,J=7Hz,4H,N—CH$_2$) 3.50(s,18H,O—CH$_3$) 4.85(br,s,1H,=⟨H⟩) 5.03(br,s,1H,=⟨H⟩) | 0.43(t,J=7Hz,4H,Si—CH$_2$) 1.53(quint,J=7Hz,4H, Si—C—CH$_2$) 3.22(t,J=7Hz,4H,N—CH$_2$) 3.50(s,18H,O—CH$_3$) 5.53(dd,J=3,11Hz,1H,=⟨H⟩) 6.17(dd,J=3,17Hz,1H,=⟨H⟩) 6.47(dd,J=11,17Hz,1H,=⟨H⟩) |
| IR | 2950(CH) 1620(C=O,C=C) 1190(Si—O—C) 1090(Si—O—C) | 2950(CH) 1640(C=O) 1610(C=C) 1180(Si—O—C) 1060(Si—O—C) | 2950(CH) 1620(C=O,C=C) 1190(Si—O—C) 1090(Si—O—C) | 2950(CH) 1620(C=O,C=C) | 2950(CH) 2850(CH) 1620(C=O,C=C) 1190(Si—O—C) 1090(Si—O—C) | 2940(CH) 2850(CH) 1640(C=O) 1610(C=C) 1180(Si—O—C) 1060(Si—O—C) |
| Mass (M$^+$) elemental analysis | 433 C 55.20(55.38) H 9.89(9.99) N 3.30(3.23) Si 12.99(12.95) | 419 C 54.09(54.37) H 9.79(9.85) N 3.45(3.34) Si 13.50(13.38) | 373 C 57.56(57.86) H 10.60(10.52) N 3.81(3.75) Si 15.21(15.03) | 433 C 27.27(27.54) H 4.08(3.93) N 3.33(3.21) Cl 48.50(48.77) Si 13.01(12.88) | 409 C 46.67(46.91) H 8.59(8.61) N 3.30(3.42) Si 13.58(13.71) | 395 C 45.40(45.54) H 8.34(8.41) N 3.29(3.54) Si 13.95(14.20) |

EXAMPLE 7

165 parts N,N-diallylmethacrylamide, 4 parts of 1% chloroplatinic acid-isopropanol solution, and 4 parts of phenothiazine were placed in a 4-necked flask equipped with a thermometer, dropping funnel, stirrer and reflux condenser provided with a calcium chloride tube, and heated to 50° C. while stirring. 161 parts of methyldiethoxysilane was dropped into the mixed solution over a time period of 30 minutes. Following this addition, the mixture is further heated while stirring at 55° C. for 2 hours to bring the reaction to completion. 168 parts of a colorless, transparent liquid was recovered from the obtained reaction mixture by using gas chromatography separation. Infrared absorption spectroscopy, nuclear magnetic resonance spectroscopy, mass spectroscopy and elemental analysis were then performed on this liquid. Those results are indicated in Table 1. Based on those measurement results, it was confirmed that the compound that was obtained was N-allyl-N-(3-methyldiethoxysilyl)propylmethacrylamide. The yield was 56%, $n_D^{25} = 1.4607$ and $d_4^{25} = 1.024$.

Figure 3:
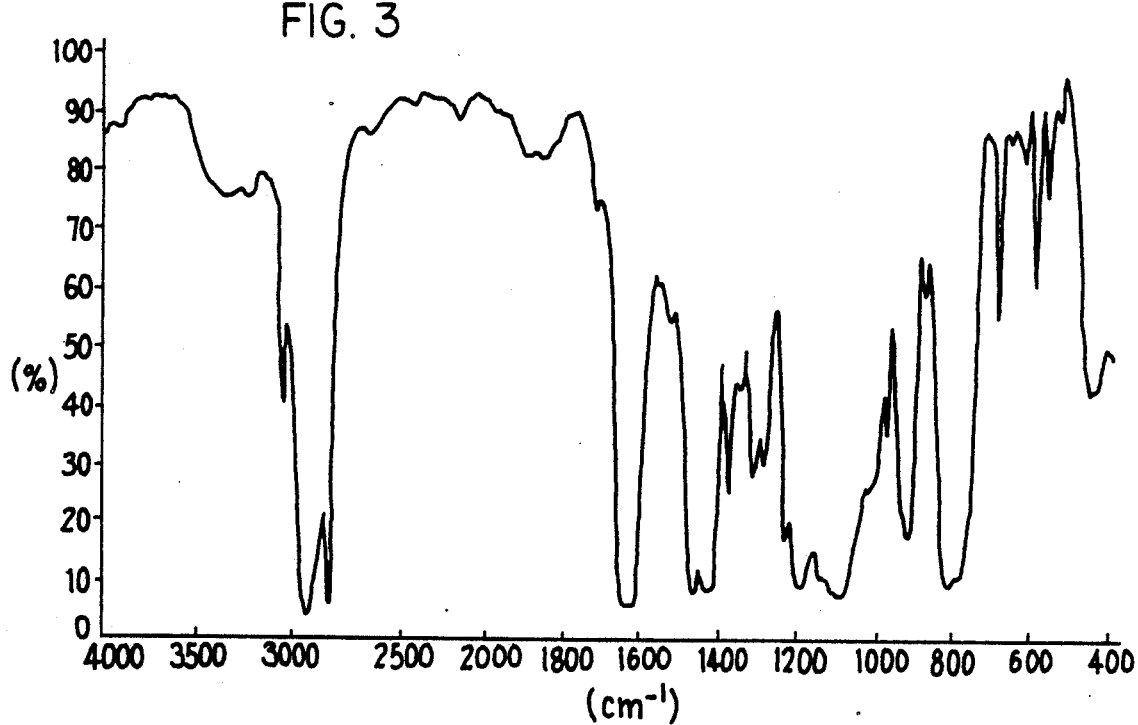
FIG. 3 is the infrared absorption spectrum of the compound prepared in Embodiment 7 and FIG. 4 is the nuclear magnetic resonance spectrum of the same compound.
Figure 4:
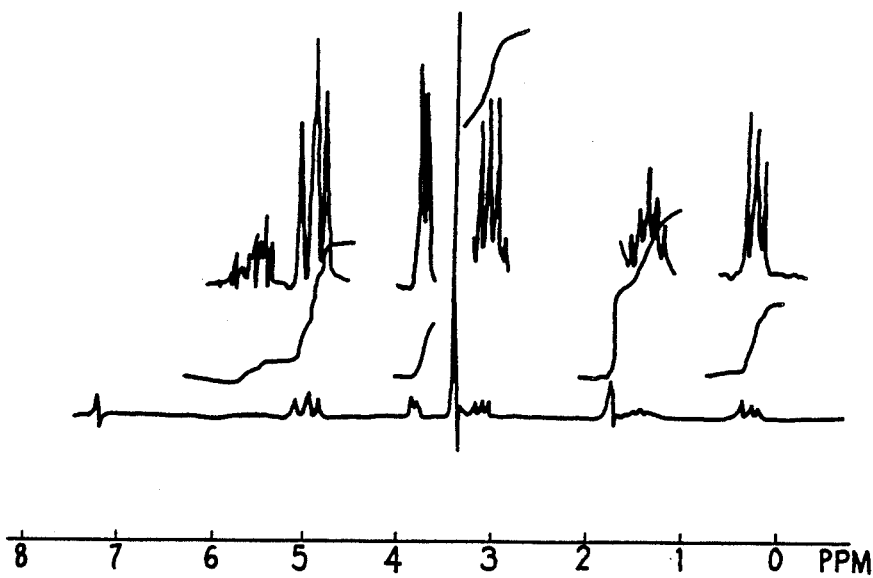

Further, the infrared absorption spectrum and nuclear magnetic resonance spectrum are indicated in FIG. 3 and FIG. 4 respectively.

EXAMPLE 8

161 parts of methyldiethoxysilane was dropped into a mixed solution of 151 parts of N,N-diallylacrylamide, 4 parts of 1% chloroplatinic acid-isopropanol solution, and 4 parts of phenothiazine and allowed to react. 146 parts of a colorless, transparent liquid was recovered from the obtained reaction mixture by using gas chromatography separation. The same measurements were performed on this liquid as those that were performed in Example 1.

Based on those results, it was confirmed that the compound that was obtained was N-allyl-N-(3-methyldiethoxysilyl)propylacrylamide. The yield was 51%.

EXAMPLE 9

125 parts of dimethylethoxysilane was dropped into a mixed solution of 165 parts of N,N-diallylmethacrylamide, 4 parts of 1% chloroplatinic acid-isopropanol solution, and 4 parts of phenothiazine and allowed to react.

135 parts of a colorless, transparent liquid was recovered from the obtained reaction mixture by using gas chromatography separation. The same measurements were performed on this liquid as those that were performed in Example 1.

Based on those results, it was confirmed that the compound that was obtained was N-allyl-N-(3-dimethylethoxysilyl)propylmethacrylamide. The yield was 50%.

EXAMPLE 10

163 parts of trichlorosilane was dropped into a mixed solution of 165 parts of N,N-diallylmethacrylamide, 4 parts of 1% chloroplatinic acid-isopropanol solution, and 4 parts of phenothiazine and allowed to react.

162 parts of a colorless, transparent liquid was recovered from the obtained reaction mixture by using gas chromatography separation. The same measurements were performed on this liquid as those that were performed in Example 1.

Based on those results, it was confirmed that the compound that was obtained was N-allyl-N-(3-trichlorosilyl)propylmethacrylamide. The yield was 54%.

EXAMPLE 11

219 parts of $\gamma$-(N-allyl)aminopropyltrimethoxysilane, 101 parts of triethyl amine, 1150 parts of anhydrous benzene and 0.4 parts of phenothiazine as a polymerization inhibitor were placed in a three-necked flask equipped with a thermometer, dropping funnel and reflux condenser to which a calcium chloride tube was attached. 105 parts of methacryloyl chloride dissolved in 250 parts of anhydrous benzene was then dropped into this mixed solution contained in an ice bath over a time period of roughly 20 minutes. The reaction temperature was 5°–15° C. After the addition was completed, the mixture was allowed to react for 2 hours at room temperature. After removing the salt that was formed from the mixture by filtration, the benzene contained in the mixture was removed by distillation in vacuo.

Further, 153 parts of a colorless, transparent liquid was recovered from the obtained oil-like substance by using gas chromatography separation. The same measurements were performed on this liquid as those that were performed in Example 1.

Based on those results, it was confirmed that the compound that was obtained was N-allyl-N-(3-trimethoxysilyl)-propylmethacrylamide. The yield was 53%.

EXAMPLE 12

91 parts of acryloyl chloride dissolved in 250 parts of anhydrous benzene was dropped into a mixture of 219 parts of $\gamma$-(N-allyl)aminopropyltrimethoxysilane, 101 parts of triethylamine, 1150 parts of anhydrous benzene and 0.4 parts of phenothiazine and allowed to react.

140 parts of a colorless, transparent liquid was recovered from the obtained oil-like substance by using gas chromatography separation. The same measurements were performed on this liquid as those that were performed in Example 1. Based on those results, it was confirmed that the compound that was obtained was N-allyl-N-(3-trimethoxysilyl)propylacrylamide. The yield was 51%.

TABLE 2

| | Example | | | | | |
|---|---|---|---|---|---|---|
| | 7 | 8 | 9 | 10 | 11 | 12 |
| NMR (90MHz, CCl$_4$,δ) | 0.04(s,3H,Si—CH$_3$) 0.30–0.53(m,2H,Si—CH$_2$) 1.20(t,J=7Hz,6H,O—C—CH$_3$) 1.33–1.75(m,2H,Si—C—CH$_2$) 1.85(s,3H, =⟨CH$_3$⟩) 3.20(t,J=7Hz,2H,N—CH$_2$) 3.80(q,J=7Hz,4H,O—CH$_2$) 3.85(d,J=6Hz,2H, ⟨CH$_2$—N⟩) 4.89–5.27(m,2H,olefinic) 5.40–6.00(m,2H,olefinic) 6.17(dd,J=3,11Hz,1H,olefinic) 6.47(dd,J=11,17Hz,1H,olefinic) | 0.04(s,3H,Si—CH$_3$) 0.30–0.53(m,2H,Si—CH$_2$) 1.20(t,J=7Hz,6H,O—C—CH$_3$) 1.33–1.75(m,2H,Si—C—CH$_2$) 3.20(t,J=7Hz,2H,N—CH$_2$) 3.80(q,J=7Hz,4H,O—CH$_2$) 3.85(d,J=6Hz,2H, ⟨CH$_2$—N⟩) 4.89–5.27(m,2H,olefinic) 5.40–6.00(m,2H,olefinic) 6.17(dd,J=3,11Hz,1H,olefinic) 6.47(dd,J=11,17Hz,1H,olefinic) | 0.04(s,6H,Si—CH$_3$) 0.30–0.53(m,2H,Si—CH$_2$) 1.20(t,J=7Hz,3H,O—C—CH$_3$) 1.33–1.75(m,2H,Si—C—CH$_2$) 1.85(s,3H, =⟨CH$_3$⟩) 3.20(t,J=7Hz,2H,N—CH$_2$) 3.80(q,J=7Hz,2H,O—CH$_2$) 3.85(d,J=6Hz,2H, ⟨CH$_2$—N⟩) 4.89–5.27(m,4H,olefinic) 5.55–6.00(m,1H,olefinic) | 0.57(t,J=7Hz,2H,Si—CH$_2$) 1.60(quint,J=7Hz,2H, Si—C—CH$_2$) 1.85(s,3H, =⟨CH$_3$⟩) 3.30(t,J=7Hz,2H,N—CH$_2$) 3.85(d,J=6Hz,2H, ⟨CH$_2$—N⟩) 4.89–5.27(m,4H,olefinic) 5.55–6.00(m,1H,olefinic) | 0.40(t,J=7Hz,2H,Si—CH$_2$) 1.53(quint,J=7Hz,2H, Si—C—CH$_2$) 1.85(s,3H, =⟨CH$_3$⟩) 3.20(t,J=7Hz,2H,N—CH$_2$) 3.50(s,9H,O—CH$_3$) 3.85(d,J=6Hz,2H, ⟨CH$_2$—N⟩) 4.89–5.27(m,4H,olefinic) 5.55–6.00(m,1H,olefinic) | 0.40(t,J=7Hz,2H,Si—CH$_2$) 1.53(quint,J=7Hz,2H, Si—C—CH$_2$) 3.20(t,J=7Hz,2H,N—CH$_2$) 3.50(s,9H,O—CH$_3$) 3.85(d,J=6Hz,2H, ⟨CH$_2$—N⟩) 4.89–5.27(m,2H,olefinic) 5.40–6.00(m,2H,olefinic) 6.17(dd,J=3,11Hz,1H,olefinic) 6.47(dd,J=11,17Hz,1H,olefinic) |
| IR (cm$^{-1}$) | 3080(C=C) 2950(CH) 1620(C=O,C=C) 1190(Si—O—C) 1090(Si—O—C) | 3080(C=C) 2950(CH) 1640(C=O) 1610(C=C) 1180(Si—O—C) 1060(Si—O—C) | 3080(C=C) 2950(CH) 1620(C=O,C=C) 1190(Si—O—C) 1090(Si—O—C) | 3080(C=C) 2950(CH) 1620(C=O,C=C) | 3080(C=C) 2940(CH) 2850(CH) 1620(C=O,C=C) 1190(Si—O—C) 1100(Si—O—C) | 3080(C=C) 2940(CH) 2850(CH) 1644(C=O) 1610(C=C) 1180(Si—O—C) 1060(Si—O—C) |
| Mass (M$^+$) elemental analysis | 299 C 59.90(60.16) H 9.59(9.71) N 4.81(4.68) Si 9.18(9.38) | 285 C 58.63(58.90) H 9.48(9.53) N 4.95(4.91) Si 9.71(9.84) | 269 C 62.33(62.42) H 9.99(10.10) N 5.27(5.20) Si 10.28(10.40) | 299 C 39.71(39.94) H 5.28(5.36) N 4.76(4.66) Cl 35.48(35.37) Si 9.21(9.34) | 287 C 54.06(54.32) H 8.69(8.77) N 4.99(4.87) Si 9.57(9.77) | 273 C 52.55(52.72) H 8.34(8.48) N 5.26(5.12) Si 10.04(10.27) |

What is claimed is:

1. An orgonosilicon compound of general formula (1):

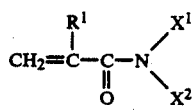

in which $R^1$ is a hydrogen atom or a methyl group, $X^1$ and $X^2$ each independently are $-CH_2CH=CH_2$ or $-(CH_2)_3SiR^2_nY_{3-n}$, provided at least one of them is $-(CH_2)_3SiR^2_nY_{3-n}$, $R^2$ is a substituted or non-substituted monovalent hydrocarbon group, Y is an alkoxy group or a halogen atom, and n is zero, 1 or 2.

2. The organic compound as claimed in claim 1, where $R^2$ is a member selected from the group consisting of an alkyl group having 1 to 6 carbon atoms, a halogenated alkyl group having 1 to 6 carbon atoms, a cycloalkyl group having 5 to 6 carbon atoms, a 2-phenylethyl group, a phenyl group, a halogenated phenyl group and a tolyl group, and Y is an alkoxy group having 1 to 4 carbon atoms or a halogen atom.

3. The compound as claimed in claim 1, wherein both $X^1$ and $X^2$ are $-(CH_2)_3SiR^2_nY_{3-n}$.

4. The organsilicon compound claimed in claim 1, wherein $R^2$ is a methyl group.

5. The compound as claimed in claim 1, wherein $X^1$ is $-CH_2CH=CH_2$ and $X^2$ is $-(CH_2)_3Sir^2_nY_{3-n}$.

6. A method of preparing an organosilicon compound of general formula (1):

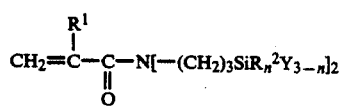

in which $R^1$ is a hydrogen atom or a methyl group, $R^2$ is a substituted or non-substituted monovalent hydrocarbon group, Y is an alkoxy group or a halogen atom, and n is zero, 1 or 2, comprising the step of carrying out an addition reaction in the presence of a catalyst between an amide compound of general formula (2):

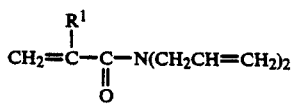

, in which $R^1$ is as indicated above, and a silane compound of general formula (3):

 (3)

in which $R^2$, Y and n are as described above.

7. A method of preparing an organosilicon compound of general formula (1):

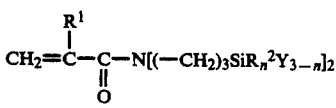

, in which $R^1$ is a hydrogen atom or a methyl group, $R^2$ is a substituted or non-substituted monovalent hydrocarbon group, Y is an alkoxy group or a halogen atom, and n is zero, 1 or 2, comprising the step of carrying out a reaction between an acid chloride of general formula (4):

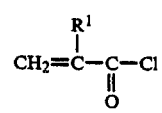

, in which $R^1$ is as described above, and a silane compound of general formula (5):

$HN_2$ (5)

, in which $R^2$, Y and n are as described above.

8. A method of preparing an organosilicon compound of general formula (1):

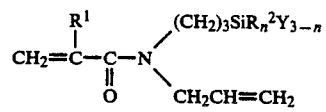

, in which $R^1$ is a hydrogen atom or a methyl group, $R^2$ is a substituted or non-substituted monovalent hydrocarbon group, Y is an alkoxy group or a halogen atom, and n is zero, 1 or 2, comprising the step of carrying out an addition reaction in the presence of a catalyst between an amide compound of general formula (2):

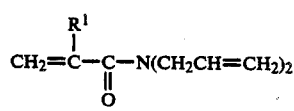

, in which $R^1$ is as described above, and a silane compound of general formula (3):

 (3)

, in which $R^2$, Y and n are described above.

9. A method of preparing an organosilicon compound of general formula (1):

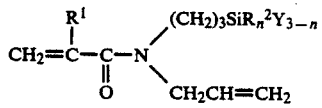

, in which $R^1$ is a hydrogen atom or a methyl group, $R^2$ is a substituted or non-substituted monovalent hydrocarbon group, Y is an alkoxy group or a halogen atom, and n is zero, 1 or 2, comprising the step of carrying out a reaction between an acid chloride of general formula (4):

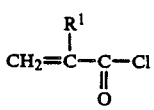

, in which $R^1$ is as described above, and a silane compound of general formula (5):

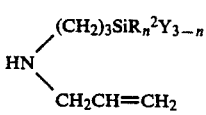

, in which $R^2$, Y and n are as described above.

* * * * *

UNITED STATES PATENT AND TRADEMARK OFFICE
CERTIFICATE OF CORRECTION

PATENT NO. : 4 990 641
DATED : February 5, 1991
INVENTOR(S) : Keiji KABETA It is certified that error appears in the above-identified patent and that said Letters Patent is hereby corrected as shown below:

On the title page at item [57], third line following the formula, change "$-(CH_2)_2SiR^2_nY_{3-n}$" to --- $-(CH_2)_3SiR^2_nY_{3-n}$ ---.

On the title page at item [57], third line following the formula, after "them" insert ---is---.

Column 17, line 35, change the right-hand portion of the formula to read as follows:

--- $-N[-(CH_2)_3SiR^2_nY_{3-n}]_2$ ---.

Column 17, line 62, change the right-hand portion of the formula to read as follows:

--- $-N[(-CH_2)_3SiR^2_nY_{3-n}]_2$ ---.

UNITED STATES PATENT AND TRADEMARK OFFICE
CERTIFICATE OF CORRECTION

PATENT NO. : 4 990 641
DATED : February 5, 1991
INVENTOR(S) : Keiji KABETA It is certified that error appears in the above-identified patent and that said Letters Patent is hereby corrected as shown below:

Column 18, line 12, change "$HN_2$" to read as follows:

$$--- HN[(CH_2)_3SiR^2_nY_{3-n}]_2 ---.$$

Column 18, line 19, change the upper portion of the right-hand portion of the formula to read as follows:

$$--- (CH_2)_3SiR^2_nY_{3-n} ---.$$

Column 18, line 31, change the right-hand portion of the formula to read as follows:

$$--- N(CH_2CH=CH)_2 ---.$$

UNITED STATES PATENT AND TRADEMARK OFFICE
CERTIFICATE OF CORRECTION

PATENT NO. : 4 990 641

DATED : February 5, 1991

INVENTOR(S) : Keiji KABETA

It is certified that error appears in the above-identified patent and that said Letters Patent is hereby corrected as shown below:

Column 18, line 43, change the upper portion of the right-hand portion of the formula to read as follows:

--- $(CH_2)_3 SiR^2_n Y_{3-n}$ ---.

Column 18, line 63, change the upper portion of the right-hand portion of the formula to read as follows:

--- $(CH_2)_3 SiR^2_n Y_{3-n}$ ---.

Signed and Sealed this

Thirteenth Day of October, 1992

*Attest:*

DOUGLAS B. COMER

*Attesting Officer*    *Acting Commissioner of Patents and Trademarks*